US010689690B2

(12) United States Patent
Costa

(10) Patent No.: US 10,689,690 B2
(45) Date of Patent: Jun. 23, 2020

(54) LIBRARY CONSTRUCTION USING Y-ADAPTERS AND VANISHING RESTRICTION SITES

(71) Applicant: Centrillion Technology Holdings Corporation, Grand Cayman (KY)

(72) Inventor: Justin Costa, Palo Alto, CA (US)

(73) Assignee: Centrillion Technology Holdings Corporation, Grand Cayman (KY)

(*) Notice: Subject to any disclaimer, the term of this patent is extended or adjusted under 35 U.S.C. 154(b) by 0 days.

(21) Appl. No.: 15/235,236

(22) Filed: Aug. 12, 2016

(65) Prior Publication Data
US 2017/0044600 A1 Feb. 16, 2017

Related U.S. Application Data

(60) Provisional application No. 62/204,943, filed on Aug. 13, 2015.

(51) Int. Cl.
| C12N 15/10 | (2006.01) |
| C40B 30/00 | (2006.01) |
| C40B 40/06 | (2006.01) |
| C12Q 1/6855 | (2018.01) |
| C12Q 1/6806 | (2018.01) |

(52) U.S. Cl.
CPC ....... *C12Q 1/6855* (2013.01); *C12N 15/1093* (2013.01); *C12Q 1/6806* (2013.01)

(58) Field of Classification Search
None
See application file for complete search history.

(56) References Cited

U.S. PATENT DOCUMENTS

| 6,287,825 | B1 | 9/2001 | Weissman et al. | |
| 8,293,503 | B2* | 10/2012 | Slater | C12N 15/10 435/320.1 |
| 9,328,382 | B2 | 5/2016 | Drmanac et al. | |
| 2002/0065609 | A1 | 5/2002 | Ashby | |
| 2007/0128624 | A1* | 6/2007 | Gormley | C12Q 1/6855 435/6.12 |
| 2010/0041561 | A1* | 2/2010 | Gormley | C12Q 1/6855 506/2 |
| 2011/0020865 | A1 | 1/2011 | Payne et al. | |
| 2014/0093916 | A1* | 4/2014 | Belyaev | C12N 9/22 435/91.2 |
| 2014/0186940 | A1 | 7/2014 | Goel | |
| 2014/0194324 | A1* | 7/2014 | Gormley | C12Q 1/6869 506/17 |
| 2014/0221217 | A1 | 8/2014 | Van Eijk et al. | |
| 2014/0329233 | A1* | 11/2014 | Minshull | C12N 15/64 435/6.1 |
| 2016/0046985 | A1 | 2/2016 | Drmanac et al. | |
| 2016/0168632 | A1 | 6/2016 | Edwards | |
| 2017/0022554 | A1 | 1/2017 | Drmanac et al. | |

FOREIGN PATENT DOCUMENTS

| WO | WO-0029616 A1 | 5/2000 | |
| WO | WO-2007010251 A2 | 1/2007 | |
| WO | WO-2007052006 A1 | 5/2007 | |
| WO | WO-2007060456 A1 | 5/2007 | |
| WO | WO-2010038042 A1 | 4/2010 | |
| WO | WO-2011085075 A2 | 7/2011 | |
| WO | WO-2012078312 A2 | 6/2012 | |
| WO | WO-2012106546 A2 | 8/2012 | |
| WO | WO-2013032850 A2 | 3/2013 | |
| WO | WO-2012106546 A3 | 11/2013 | |
| WO | WO-2015017759 A1 | 2/2015 | |
| WO | WO-2015104302 A1 * | 7/2015 | ........... C12Q 1/6827 |
| WO | WO-2015179790 A1 | 11/2015 | |
| WO | WO-2017027779 A1 | 2/2017 | |

OTHER PUBLICATIONS

Kurosawa et al. (Journal of electrostatics 65.7 (2007): 423-430.).*
Ansorge, W., "Next-generation DNA sequencing techniques," New Biotech., 25(4):195-203, 2009.
Dimalanta, E. T., et al., "A microfluidic system for large DNA molecule arrays," Anal. Chem., 76(18):5293-301, 2004.
Engler et al., The Enzymes, 15: 3-29, 1982.
Ferree, S., et al., "Electrokinetic stretching of tethered DNA," Biophys. J., 85(4):2539-46, 2003.
Higgins et al., Methods in Enzymology, 68: 50-71, 1979; .
International search report with written opinion dated Nov. 4, 2016 for PCT/US16/46697.
Kaji, N., "Molecular stretching of long DNA in agarose gel using alternating current electric fields," Biophys. J., 82(1 Pt 1):335-44, 2002.
Kurosawa et al. "Dissection, acquisition and amplification of targeted position of electrostatically stretched DNA," J Electrostatics, Feb. 20, 2007 (Feb. 20, 2007), vol. 65, No. 7, pp. 423-430.
Perkins, T. T., et al., "Stretching of a single tethered polymer in a uniform flow," Science, 268: 83-7, 1995.
Randall, G. C.., et al., "Methods to electrophoretically stretch DNA: microconstractions, gels, and hybrid gel-microconstraction devices," Lab. Chip, 6(4):516-25, 2006.
Shendure, J. and Ji, H., "Next-generation DNA sequencing," Nature Biotech., 26:1135-45, 2008.

(Continued)

*Primary Examiner* — Tracy Vivlemore
*Assistant Examiner* — Sahana S Kaup
(74) *Attorney, Agent, or Firm* — Wilson, Sonsini, Goodrich & Rosati

(57) ABSTRACT

The present disclosure describes systems and methods to construct genomic DNA fragments library by stretching genomic DNA over an adapter-modified chip; using an enzyme cocktail comprising a first restriction enzyme, a ligase, and a second restriction enzyme to cut the genomic DNA into fragments and ligate the fragments to the adapters on the chip; and amplifying thus-obtained DNA by PCR amplification.

20 Claims, 9 Drawing Sheets

Specification includes a Sequence Listing.

(56) References Cited

OTHER PUBLICATIONS

Shendure, J., et al., "Advanced sequencing technologies: methods and goals," Nat. Rev. Genet., 5(5):335-44, 2004.
Sitters, G., et al., "Acoustic force spectroscopy," Nat. Methods, 12(1):47-50, 2015.
Smith, S. B., et al., "Overstretching B-DNA: the elastic response of individual double-stranded and single-stranded DNA molecules," Science, 271: 795-9, 1996.
Tegenfeldt, J. O., et al., "The dynamics of genomic-length DNA molecules in 100-nm channels," Proc. Natl. Acad. Sci. U. S. A., 101(30):10979-83, 2004.
Wong, P. K., et al., "Deformation of DNA molecules by hydrodynamic focusing," J. Fluid. Mech., 497:55-65, 2003.
Xu, et al. Nucleic Acids Research, 27: 875-881, 1999; .
European Search Report dated Jan. 18, 2017 for EP Application No. 16184098.8-1404.
EP16184098.8 Office Action dated Jul. 18, 2018.
EP 16184098.8 Office Action dated Feb. 9, 2018.

\* cited by examiner

FIG. 15
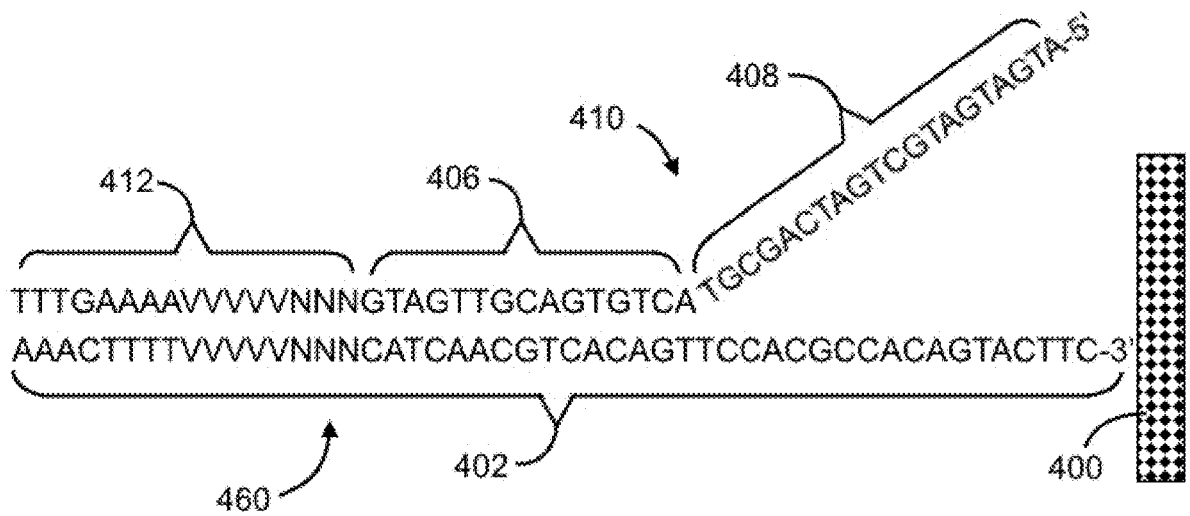
FIG. 16
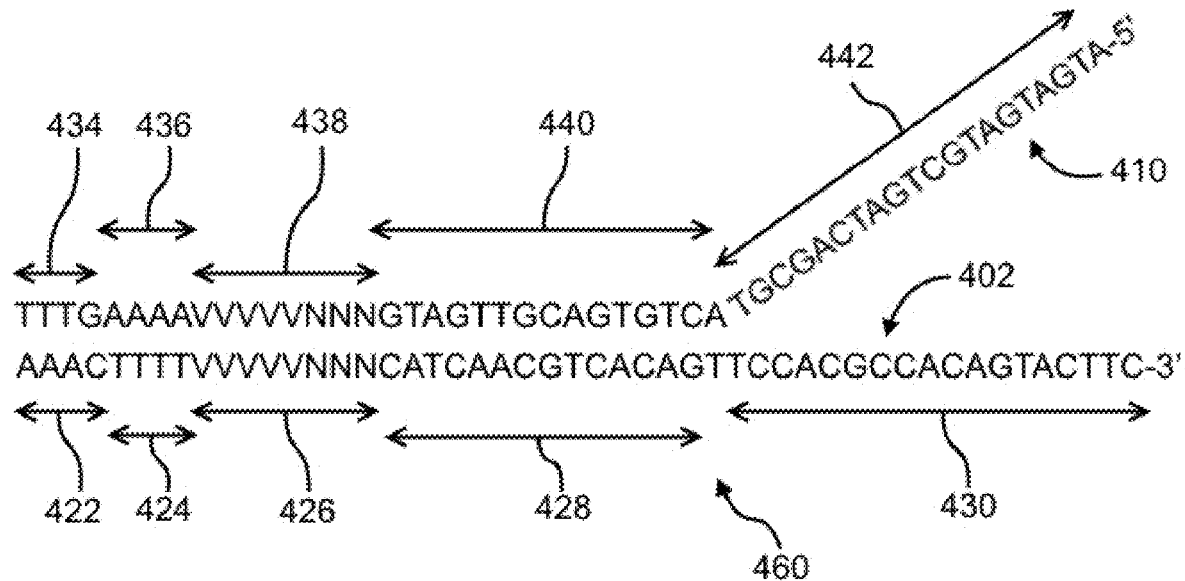
FIG. 17
5'—FC2—SEQ B'—SEQ A'—Barcode 1—Genomic DNA'—Barcode 2'—SEQ A—SEQ C'—FC1'—3'
3'—FC2'—SEQ B—SEQ A—Barcode 1'—Genomic DNA—Barcode 2—SEQ A'—SEQ C—FC1—5'

Lane 1　　Lane 2

Lane 3

LIBRARY CONSTRUCTION USING Y-ADAPTERS AND VANISHING RESTRICTION SITES

CROSS-REFERENCE

This application claims the benefit of U.S. Provisional Patent Application No. 62/204,943, filed on Aug. 13, 2015, which is entirely incorporated herein by reference.

SEQUENCE LISTING

The instant application contains a Sequence Listing which has been filed electronically in ASCII format and is hereby incorporated by reference in its entirety. Said ASCII copy, created on Aug. 9, 2016, is named 38558-727_601_SL.txt and is 1,616 bytes in size.

BACKGROUND OF THE INVENTION

Strategies for DNA sequencing may be grouped into several categories. (Shendure, J., et al., "Advanced sequencing technologies: methods and goals," Nat. Rev. Genet., 5(5):335-44, 2004). They include (i) microelectrophoretic methods, (ii) sequencing by hybridization, (iii) real-time observation of single molecules, and (iv) cyclic-array sequencing. Available commercial products include 454 sequencing (used in the 454 Genome Sequencers, Roche Applied Science; Basel), Solexa technology (used in the Illumina (San Diego) Genome Analyzer), the SOLiD platform (Applied Biosystems; Foster City, Calif., USA), the Polonator (Dover/Harvard), and the HeliScope Single Molecule Sequencer technology (Helicos; Cambridge, Mass., USA).

One commonality of these sequencing techniques is the generation of a library from biological samples. Library preparation is accomplished by random fragmentation of DNA samples, followed by in vitro ligation of common adapter sequences. Further, what is common to these methods is that PCR amplicons derived from any given single fragmented DNA molecule in a library end up spatially clustered, either to a single location on a planar substrate (for example, in situ polonies, bridge PCR), or to the surface of micron-scale beads (for example, emulsion PCR).

New sequencing methods, commonly referred to as Next Generation Sequencing (NGS) technologies, may deliver fast, inexpensive and accurate genome information regarding biological samples through sequencing technologies. For example, high throughput NGS (HT-NGS) methods may allow scientists to obtain the desired sequencing information with greater speed, at lower cost and with acceptable error rate. One preliminary step for NGS is to prepare a nucleic acid library of the biological sample in such a way that is amenable to NGS technologies, for example, a library of short sequences with barcodes. Thus, there is a need to find new methods to construct barcoded library for sequencing purposes.

SUMMARY OF THE INVENTION

The present disclosure provides methods and systems for constructing barcoded nucleic acid libraries. For example, the present disclosure generally provides methods and systems for the preparation of barcode sequencing libraries. Such libraries can be useful with approaches employing NGS. Sequencing libraries produced as described herein relying on Y-adapters on chips, vanishing and appearing restriction sites, a cocktail of enzymes, and PCR cycles.

An aspect of the present disclosure provides a method for constructing a library from a nucleic acid, the method comprising: placing at least one copy of a nucleic acid on a surface to which are attached a plurality of adapters; applying a solution to the surface, the solution comprising: a first restriction enzyme capable of digesting the nucleic acid into a plurality of nucleic acid fragments; a ligase capable of ligating an end of one of the nucleic acid fragments with one of the adapters; and a second restriction enzyme capable of digesting self-ligated adapters among the plurality of adapters; and forming a first library, the first library comprising a plurality of ligated nucleic acid fragments having one of the adapters ligated to each end thereof.

In some embodiments of aspects provided herein, the step of placing at least one copy of a nucleic acid on a surface comprises stretching at least one copy of the nucleic acid on the surface. In some embodiments of aspects provided herein, the surface comprises acrylamide gel. In some embodiments of aspects provided herein, the surface is a solid support. In some embodiments. In some embodiments of aspects provided herein, each of the Y-shaped adapter is a partially double-stranded Y-shape oligonucleotide adapter comprising a first ligatable end, and a second unpaired end comprising two non-complementary strands, wherein the length of the non-complementary strands is at least about 8 nucleotides. In some embodiments of aspects provided herein, the plurality of adapters comprise a plurality of first adapters and a plurality of second adapters, wherein the first adapter and the second adapter are different. In some embodiments of aspects provided herein, concentration of the first restriction enzyme is higher than concentration of the ligase in the solution. In some embodiments of aspects provided herein, the concentration of the first restriction enzyme is at least two times the concentration of the ligase. In some embodiments of aspects provided herein, the ligated nucleic acid fragments are no more than 600 base pairs in length. In some embodiments of aspects provided herein, the ligated nucleic acid fragments are no more than 400 base pairs in length.

In some embodiments of aspects provided herein, the self-ligated adapters comprise a restriction site for the second restriction enzyme after the self-ligation. In some embodiments of aspects provided herein, the first restriction enzyme is type-II restriction endonuclease. In some embodiments of aspects provided herein, the first restriction enzyme recognizes 4 base pairs restriction site, 5 base pairs restriction site, or 6 base pairs restriction site. In some embodiments of aspects provided herein, the first restriction enzyme recognizes 4 base pairs restriction site. In some embodiments of aspects provided herein, the first restriction enzyme is MspA1I restriction endonuclease, PsiI restriction endonuclease, or Alu1 restriction endonuclease. In some embodiments of aspects provided herein, the first restriction enzyme is Alu1 restriction endonuclease. In some embodiments of aspects provided herein, the ligase is T4 ligase. In some embodiments of aspects provided herein, the second restriction enzyme recognizes a restriction site of at least 8 base pairs in length. In some embodiments of aspects provided herein, the first restriction enzyme recognizes a shorter sequence for the restriction site than the second restriction enzyme. In some embodiments of aspects provided herein, the second restriction enzyme is Pme1 restriction endonuclease. In some embodiments of aspects provided herein, the method further comprises amplification of the first library, thereby producing a second library of amplified ligated nucleic acid fragments. In some embodiments of aspects provided herein, the adapters include a sequence segment that functions as a molecular barcode. In some embodiments of aspects provided herein, each adapter has a unique molecular barcode that identifies the position of the adapter on the surface, and wherein the molecular barcode is included as part of the ligated nucleic acid fragment. In some embodiments of aspects provided herein, the adapter comprises a ligatable end that consists of one half of a restriction site for the second restriction enzyme. In some embodiments of aspects provided herein, the ligated nucleic acid fragments do not include a restriction site for either the first restriction enzyme or the second restriction enzyme.

Another aspect of the present disclosure provides a system to construct a library from a nucleic acid, the system comprising: a surface to which are attached a plurality of adapters; a first restriction enzyme capable of digesting the nucleic acid into a plurality of nucleic acid fragments; a ligase capable of ligating an end of one of the nucleic acid fragments with one of the adapters; and a second restriction enzyme capable of digesting self-ligated adapters among the plurality of adapters.

In some embodiments of aspects provided herein, the plurality of adapters are Y-shaped adapters. In some embodiments of aspects provided herein, concentration of the first restriction enzyme is more than concentration of the ligase. In some embodiments of aspects provided herein, the first restriction enzyme is type-II restriction endonuclease. In some embodiments of aspects provided herein, the first restriction enzyme recognizes 4 base pairs restriction sites, 5 base pairs restriction sites, or 6 base pairs restriction sites. In some embodiments of aspects provided herein, the first restriction enzyme recognizes 4 base pairs restriction sites. In some embodiments of aspects provided herein, the first restriction enzyme recognizes a shorter sequence for the restriction site than the second restriction enzyme. In some embodiments of aspects provided herein, the first restriction enzyme is MspA1I restriction endonuclease, PsiI restriction endonuclease, or Alu1 restriction endonuclease. In some embodiments of aspects provided herein, the ligase is T4 ligase. In some embodiments of aspects provided herein, the second restriction enzyme is Pme1 restriction endonuclease. In some embodiments of aspects provided herein, the adapters include a sequence segment that functions as a molecular barcode. In some embodiments of aspects provided herein, each adapter has a unique molecular barcode that identifies the position of the adapter on the surface. In some embodiments of aspects provided herein, the adapter comprises a ligatable end that consists of one half of a restriction site for the second restriction enzyme.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

A better understanding of the features and advantages of the present invention will be obtained by reference to the following detailed description that sets forth illustrative embodiments, in which the principles of the invention are utilized, and the accompanying drawings of which:

FIG. 15 displays the Y-adapter primer (SEQ ID NO: 5) in FIG. 14 extended through the backbone (SEQ ID NO: 3) according to the present disclosure.

FIG. 16 illustrates the anatomy of the complete Y-adapter in FIG. 15 according to the present disclosure. Backbone disclosed as SEQ ID NO: 3 and primer disclosed as SEQ ID NO: 5.

FIG. 17 depicts two exemplary PCR products after genomic DNA digestion and ligation with Y-adapters according to the present disclosure.

DETAILED DESCRIPTION OF THE INVENTION

Figure 1:
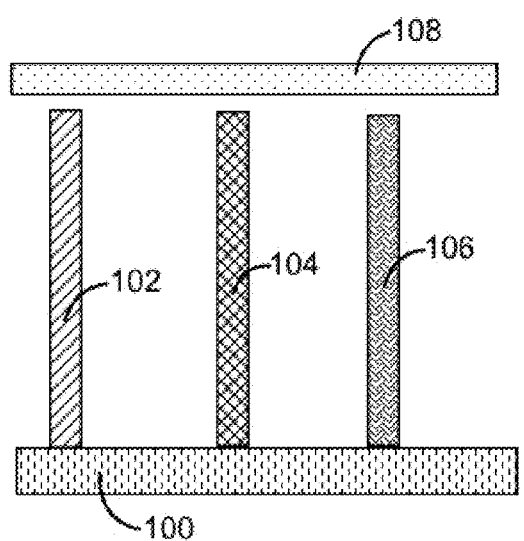
FIG. 1 illustrates a schematic drawing of the initial setup for genomic library construction using vanishing and appearing restriction site ligation according to the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

Nucleotide sequence information is the foundation on which scientists and researchers improve humans' lives either through clinical means or by material means, e.g. improving crop production, creating better fuel, making a better vaccine, creating more effective pharmaceuticals, preventing disease, or preventing an outbreak of a dangerous pathogen. (See, Ansorge, W., "Next-generation DNA sequencing techniques," *New Biotech.*, 25(4):195-203, 2009). Many parallel DNA sequencing platforms have become available and reduced the cost of DNA sequencing dramatically. NGS may accelerate biological and biomedical research, by enabling the comprehensive analysis of genomes, transcriptomes and interactomes to the next level. (See, Shendure, J. and Ji, H., "Next-generation DNA sequencing," *Nature Biotech.*, 26:1135-45, 2008). One challenge for NGS is to develop robust protocols for generating sequencing libraries, for example, barcoded libraries.

The input material for commonly used NGS sequencing platforms, such as the Illumina Genome Analyzer, the Roche (454) Genome Sequencer, the Life Technologies SOLiD platform, and 'real-time' sequencers such as Pacific Biosciences, requires libraries of DNA fragments derived from a biological sample. The DNA fragments are flanked by platform-specific adapters. Standard methods for constructing such libraries are entirely in vitro and typically include fragmenting sample DNA's (either mechanically or enzymatically), end-polishing, ligating adapter sequences, selecting fragment size, and amplifying by PCR.

After much effort in experimentation, Applicant has found new methods and systems for preparation of sequencing libraries. Sequencing libraries produced as described herein using Y-adapters on chips, vanishing and appearing restriction sites, a cocktail of enzymes, and multiple PCR cycles. In some embodiments, the sequencing libraries tagged with molecular barcodes are suitable for use in NGS reactions.

I. DEFINITIONS

All terms are intended to be understood as they would be understood by a person skilled in the art. Unless defined otherwise, all technical and scientific terms used herein have the same meaning as commonly understood by one of ordinary skill in the art to which the invention pertains. The following definitions supplement those in the art and are directed to the present disclosure and are not to be imputed to any related or unrelated case, e.g., to any commonly owned patent or application. Although any methods and materials similar or equivalent to those described herein can be used in the practice for testing of the present invention, the preferred materials and methods are described herein. Accordingly, the terminology used herein is for the purpose of describing particular embodiments only, and is not intended to be limiting.

As used in this specification and the appended claims, the singular forms "a," "an" and "the" include plural referents unless the context clearly dictates otherwise. Thus, for example, reference to "a molecule" includes a plurality of such molecules, and the like.

The term "fragment" as used herein generally refers to a fraction of the original DNA sequence or RNA sequence of the particular region.

The term "nucleic acid sequence" or "nucleotide sequence" as used herein refers to nucleic acid molecules with a given sequence of nucleotides, of which it may be desired to know the presence or amount. The nucleotide sequence can comprise ribonucleic acid (RNA) or DNA, or a sequence derived from RNA or DNA. Examples of nucleotide sequences are sequences corresponding to natural or synthetic RNA or DNA including genomic DNA and messenger RNA. The length of the sequence can be any length that can be amplified into nucleic acid amplification products, or amplicons, for example up to about 20, 50, 100, 200, 300, 400, 500, 600, 700, 800, 1,000, 1,200, 1,500, 2,000, 5,000, 10,000 or more than 10,000 nucleotides in length.

The term "template" as used herein refers to individual polynucleotide molecules from which another nucleic acid, including a complementary nucleic acid strand, may be synthesized by a nucleic acid polymerase. In addition, the template may be one or both strands of the polynucleotides that are capable of acting as templates for template-dependent nucleic acid polymerization catalyzed by the nucleic acid polymerase. Use of this term should not be taken as limiting the scope of the present disclosure to polynucleotides which are actually used as templates in a subsequent enzyme-catalyzed polymerization reaction. Further, a template may contain sequences not complementary to the desired amplification products for various reasons known by a person of ordinary skill in the art.

The term "PCR" or "Polymerase chain reaction" as used herein refers to the well-known technique of enzymatic replication of nucleic acids which uses thermal cycling for example to denature, extend and anneal the nucleic acids.

Two polynucleotides "hybridize" when they associate to form a stable duplex, e.g., under relevant assay conditions. Nucleic acids hybridize due to a variety of well characterized physico-chemical forces, such as hydrogen bonding, solvent exclusion, base stacking and the like. An extensive guide to the hybridization of nucleic acids is found in Tijssen (1993) Laboratory Techniques in Biochemistry and Molecular Biology-Hybridization with Nucleic Acid Probes, part I chapter 2, "Overview of principles of hybridization and the strategy of nucleic acid probe assays" (Elsevier, New York)

The term "about" or "nearly" as used herein generally refers to within +/−15%, 10%, 9%, 8%, 7%, 6%, 5%, 4%, 3%, 2%, or 1% of the designated amount.

The term "complementary" as used herein refers to a polynucleotide that forms a stable duplex with its "complement," e.g., under relevant assay conditions. Typically, two polynucleotide sequences that are complementary to each other have mismatches at less than about 20% of the bases, at less than about 10% of the bases, preferably at less than about 5% of the bases, and more preferably have no mismatches.

A "polynucleotide sequence" or "nucleotide sequence" or "a sequence of a nucleic acid" as used herein refers to a polymer of nucleotides (an oligonucleotide, a DNA, a nucleic acid, etc.) or a character string representing a nucleotide polymer, depending on context. From any specified polynucleotide sequence, either the given nucleic acid or the complementary polynucleotide sequence (e.g., the complementary nucleic acid) can be determined.

The term "digesting" or "digestion," as used herein when associated with restriction enzymes, refers to the controlled decomposition of DNA, which is effected using restriction endonucleases with known recognition and/or cleavage sites. Restriction endonucleases are enzymes that cleave the sugar-phosphate backbone of DNA, usually both strands of double-stranded DNA within a stretch of just a few bases. Several thousand different restriction endonucleases have been isolated, which collectively exhibit a few hundred different sequence specificities.

As used herein when associated with restriction enzymes, "restriction site" or "restriction recognition site" or "recognition site" is a location on a DNA molecule containing specific (for example, 4-8 base pairs in length) sequences of nucleotides, which are recognized by restriction enzymes to digest or cut.

"Ligation" as used herein refers to the formation of a covalent bond or linkage between the termini of two or more nucleic acids, e.g. oligonucleotides and/or polynucleotides. The nature of the bond or linkage may vary widely and the ligation may be carried out enzymatically or chemically. As used herein, ligations are usually carried out enzymatically to form a phosphodiester linkage between a 5' phosphate of a terminal nucleotide of one oligonucleotide with 3' hydroxyl of another oligonucleotide. A variety of template-driven ligation reactions are described in the following references, which are incorporated by reference: Xu and Kool, *Nucleic Acids Research,* 27: 875-881, 1999; Higgins et al., *Methods in Enzymology,* 68: 50-71, 1979; Engler et al., *The Enzymes,* 15: 3-29, 1982.

The term "DNA polymerase" as used herein refers to a cellular or viral enzyme that synthesizes DNA molecules from their nucleotide building blocks.

The term "array" as used herein, when describing a device, a system, sensors, sample chambers, etc., refers to a one-dimensional or two-dimensional set of microstructures. An array may be any shape. For example, an array may be a series of microstructures arranged in a line, such as the array of squares. An array may be arranged in a square or rectangular grid. There may be sections of the array that are separated from other sections of the array by spaces. An array may have other shapes. For example, an array may be a series of microstructures arranged in a series of concentric circles, in a series of concentric squares, a series of concentric triangles, a series of curves, etc. The spacing between sections of an array or between microstructures in any array may be regular or may be different between particular sections or between particular pairs of microstructures. The microstructure arrays of the present invention may be comprised of microstructures having zero-dimensional, one-dimensional or two-dimensional shapes. The microstructures having two-dimensional shapes may have shapes such as squares, rectangles, circles, parallelograms, pentagons, hexagons, irregular shapes, etc.

II. METHODS AND SYSTEMS

The present disclosure provides methods, devices, and systems to enable construction of barcoded nucleic acid libraries. The methods, device, and systems of the present disclosure can comprise components including, but not limited to:

1. Chip, which comprises a solid or semi-solid substrate for the attachment of Y-adapters. The substrate may comprise one or more layers made of the same or different materials, such as metals, glass, semiconductors, synthetic or natural materials, and organic or inorganic materials. Non-limiting examples of materials that can be used to form the substrate may comprise glass, quartz, silicon, a silicon-based material (e.g., silicon nitride or silica), a metal, plastics, polymeric materials (e.g., thermoset, elastomer, thermoplastic, polystyrene, nylon, polydopamine (PDA), polyvinyl chloride (PVC), poly(dimethylsiloxane) (PDMS), polyvinylidene fluoride etc.), paper, hydrogel, or a combination thereof. The substrate can take various shapes, 1-, 2-, or 3-dimensional, such as sheet, sphere, cube, cuboid, cone, cylinder, prism, pyramid, tube, plate, disc, rod, or any regular or irregular shapes. In addition, the chip may comprise millions of micron-scale features, each of which can further be attached to a Y-adapter.

The substrate may further comprise a surface. The surface of the substrate may be a flat surface, a curve surface, or a surface with raised and/or depressed regions which may facilitate the implementation of the methods of the present disclosure. The raised/depressed regions on the surface can be continuous, semi-continuous, or discontinuous. In some cases, the surface of the substrate may have alternating raised and depressed regions (e.g., a well which may retain solvents, reagents suitable for performing the methods of the present disclosure). In some cases, the surface of the substrate is divided into a number of separate sections and each individual section comprises a plurality of distinct locations, each of which can retain a polymeric molecule, such as polynucleic acid.

The surface of the substrate may be modified to facilitate or aid in the generation or synthesis of such polymers. For example, in cases where photolithographic techniques are employed, the substrate surface can be modified with photolabile protecting groups. Once the surface is illuminated through a photolithographic mask, reactive hydroxyl groups can be yielded in the illuminated regions and a monomer or a subunit of polymeric molecules can be attached thereon. By consecutively adding a monomer or a subunit to a preexisting strand, polymeric molecules are synthesized. In one example, a 3' activated deoxynucleoside, protected at the 5' hydroxyl with a photolabile group, is provided to the surface such that coupling occurs at sites that had been exposed to light. The protection at 5'-end of the deoxynucleoside is to prevent subsequent unwanted (photo) chemical reactions. The selective photodeprotection and coupling cycles can be reiterated until the desired set of probes is obtained. A variation of this process may use polymeric semiconductor photoresists, which are selectively patterned by photolithographic techniques, rather than using photolabile 5' protecting groups. In some cases, a photo-activated protective group is used as each monomer or subunit is added. Such photo-activated protective group is of itself sensitive to light and can be activated upon exposure to light.

2. Y-adapters, which are adapters with two DNA strands, part of which are not complementary to each other, thereby forming a fork of single-stranded DNA arms. The non-complementary arms of the Y-adapter can contain different elements such as identifiers, sequencing adapters, primer binding sites etc. On the top end of the Y-shape, one arm of the Y is different from the other arm of the Y. The bottom end of the Y-shape is double stranded (i.e. contains complementary strands). As used herein, Y-adapter and Y-shaped adapters are the same.

The attachment of the adapters to DNA fragments is effected by ligating the Y-adapters to one or both 5'- or 3'-ends of the DNA fragments and then optionally carrying out an initial primer extension reaction, in which extension products complementary to the immobilized oligonucleotides are formed. This step optionally comprises an amplification step for multiplying the adapter-fragment-constructs. The forked or Y-adapters can be ligated to both ends of the DNA fragments by a DNA ligase. Only the double-stranded bottom end of the Y-adapter is able to ligate to the fragments DNA.

For use in the present invention, the Y-adapter DNA is ligated to both ends of the double stranded DNA fragments, wherein one strand of the adapter DNA is ligated to one 5'-end of the DNA fragment and the other strand thereof is ligated to the respective 3' end of the DNA fragment, and this happens on both sides of the DNA fragment. The sequence of the Y-adapter can be determined by considering various factors, including but not limited to, the type of DNA sequencing technology or system used for the DNA fragments library; and the primers used for PCR process after or during the construction of the DNA fragments library.

3. Enzyme cocktail, which comprises a first restriction enzyme which digests DNA molecules into fragments; a ligase which ligates DNA fragments to the double-stranded ends of Y-adapter; and a second restriction enzyme which cuts self-ligated Y-adapters. The first restriction enzyme differs from the second restriction enzyme in that the former recognize a shorter sequence for the restriction site than the latter. Further, when used together in an enzyme cocktail in the presence of genomic DNA and Y-adapters, the first restriction enzyme can cut genomic DNA more often than the second restriction enzyme; and the second restriction enzyme can cut self-ligated Y-adapter more often than the first restriction enzyme. This can be achieved, for example, by the design of the Y-adapter such that when self-ligated, the ligated joint forms the restriction site of the second restriction enzyme.

Once a restriction endonuclease encounters its specific recognition sequence on a DNA molecule, it will bind to the DNA molecule and make a cut in one or both of the two sugar-phosphate backbones of the double helix. The positions of this cut/these cuts are determined by the identity of the restriction endonuclease. Once the DNA molecule has been cleaved at least one position, it will break into fragments. Restriction endonucleases either cut the DNA backbone symmetrically and leave blunt ends or cleave the DNA backbones in positions that are not directly opposite to each other leading to single-stranded ends (sticky ends). In any case and with the exception of the potential sticky ends, the DNA fragments created by the restriction endonuclease are double-stranded.

In one embodiment, care must be taken to make sure that the same restriction site for the first restriction enzyme should reappear after the ligation of DNA fragments. In another embodiment, similar care should be taken regarding the self-ligation of adapters and digestion thereof in that the adapters, when self-ligated, present a restriction site for the second restriction enzyme; the self-ligated adapters, after digestion by the second restriction enzyme, change back to the original adapters again.

In one embodiment, the first restriction enzyme recognizes a shorter restriction site than the second restriction enzyme. In another embodiment, the first restriction enzyme recognizes a restriction site of 4 base-pairs (bp). In one embodiment, the first restriction enzyme recognizes a restriction site of 5 bp or 6 bp. The choice of length for the restriction site depends on the desired size of the inserted DNA fragments because the frequency by which a Class II restriction enzyme cuts a DNA substrate is mainly a function of the length of the restriction site the enzyme is sensitive to. A longer restriction site for a restriction enzyme leads to lower probability of having a site for the enzyme to digest at any point in a DNA strand. In theory, an enzyme recognizing a 4 bp restriction site would lead to an average size of 256 bp for the DNA fragments after digesting. An enzyme recognizing 5 bp or 6 bp restriction site may lead to DNA fragments larger than 256 bp on average, i.e., 1,016 bp and 4,064 bp on average, respectively. In one embodiment, the first restriction enzyme leaves a blunt end on the DNA substrate after digesting. In another embodiment, the second restriction enzyme may recognize an 8 bp or longer restriction site. In theory, an enzyme recognizing an 8 bp restriction site would lead to an average size of 65,536 for the DNA fragments after digesting. In another embodiment, the second restriction enzyme leaves a blunt end on the DNA substrate after digesting.

A sticky end after digesting by either the first or the second restriction enzyme requires special treatment of the DNA products after digesting. For example, a special ligase is engaged to form covalent bonds between two sticky ends of DNA sequences, be it from the DNA fragments or adapters.

In one embodiment, the design of the adapters is such that after ligating an adapter with a DNA fragment, the ligated product, i.e., the adapter-DNA fragment, does not present a restriction site for the first restriction enzyme. In another embodiment, the ligated product, i.e., the adapter-DNA fragment, does not present a restriction site for the second restriction enzyme. In still another embodiment, the self-ligated adapters present a restriction site for the second restriction enzyme.

In one embodiment, the first restriction enzyme is MspA1I restriction enzyme. In another embodiment, the first restriction enzyme is PsiI restriction enzyme. In one embodiment for the enzyme cocktail, the first restriction enzyme is Alu1 which is a 4 bp cutting restriction enzyme and which can cut genomic DNA into fragment of, for example, about 256 bp in length. It recognizes 5'-AGACT-3' sites and cuts best at 37° C. in Cutsmart buffer supplemented with 10 mM ATP. In one embodiment, the ligase is T4 DNA ligase, which can catalyzes the covalent bond formation of two strands of DNA between the 5"-phosphate and the 3"-hydroxyl groups of adjacent nucleotides in either a cohesive-ended or blunt-ended configuration. In one embodiment, the concentration of the first restriction enzyme is higher than that of the ligase. In another embodiment, the concentration of the first restriction enzyme is about 1.1, 1.2, 1.3, 1.4, 1.5, 1.6, 1.7, 1.8, 1.9, 2.0, 3.0, 5.0, or 10.0 times that of the ligase. In still another embodiment, the concentration of the first restriction enzyme is at least 1.2, 1.3, 1.4, 1.5, 2, 3, 4, 5, 6, 7, 8, 9, 10, 20, or 30 times that of the ligase. In one embodiment, the concentration of the ligase is higher than that of the second restriction enzyme. In another embodiment, the concentration of the ligase is about 1.1, 1.2, 1.3, 1.4, 1.5, 1.6, 1.7, 1.8, 1.9, or 2.0 times that of the second restriction enzyme. In still another embodiment, the concentration of the ligase is at least 2, 3, 4, 5, 6, 7, 8, 9, 10, 20, or 30 times that of the second restriction enzyme. In one embodiment, the ratio of enzymes is 3:2:1 for the first restriction enzyme:ligase:the second restriction enzyme.

In one embodiment, the second restriction enzyme recognizes an 8 bp restriction site. In another embodiment, the second restriction enzyme recognizes a restriction site of at least 8 bp in length. In one embodiment, the second restriction enzyme is Pme1, which recognizes 5'-GTTTAAAAC-3' sites. Pme1 is sensitive to methylation. In addition, Pme1 cuts genomic DNA at a much reduced frequency when in the presence of alternative available recognition sites containing the 5'-GTTTAAAC-3' sequence. Therefore, if the Y-adapter's double-stranded end contains 3'-TTTG and 5'-AAAC, respectively, on each strand, then the self-ligated products between different Y-adapters can form the restriction site recognized by Pme1, and the self-ligated Y-adapters can be cut by Pme1. Because the low frequency for a genomic DNA to contain the 8-bp restriction site for Pme1, Pme1 very rarely cuts the genomic DNA. Even if the genomic DNA is cut by Pme1, the ligase of the enzyme cocktail can repair the cut or ligate the resulting DNA fragment with Y-adapters.

Although the above example describes one embodiment of the enzyme cocktail to include Alu1 restriction enzyme, T4 DNA ligase, and Pme1 restriction enzyme; other combinations for the enzyme cocktail are possible.

In one embodiment, a genomic DNA library comprising DNA fragments is formed by using a Y-adapter vanishing and appearing restriction site method disclosed herein. The method comprises at least three steps:

1) Stretch genomic DNA on Y-adapter chip;
2) Incubate stretched genomic DNA on Y-adapter chip with an enzyme cocktail; and
3) Conduct multiple cycles of PCR.

Referring now to the drawings, and with specific reference to FIG. 1, there is depicted an exemplary setup for genomic library construction using vanishing and appearing restriction site ligation wherein various embodiments of the present disclosure may be utilized. On the surface of chip 100 there are multiple adapters 102, 104 and 106, which are capable of ligating with a DNA fragment. On top of adapters 102, 104 and 106 there is an extended form of DNA 108, which can be a stretched genomic DNA on the surface of adapter modified chip 100.

The genomic DNA may be stretched by all kinds of means, including but not limited to, using alternating current (AC) electric fields (Kaji, N., "Molecular stretching of long DNA in agarose gel using alternating current electric fields," *Biophys. J.,* 82(1 Pt 1):335-44, 2002), using an electric field gradients in a phyperbolic contraction microchannel (Randall, G. C., et al., "Methods to electrophoretically stretch DNA: microconstractions, gels, and hybrid gel-microconstraction devices," *Lab. Chip,* 6(4):516-25, 2006), with optical tweezers uniform flows (Smith, S. B., et al., "Overstretching B-DNA: the elastic response of individual double-stranded and single-stranded DNA molecules," *Science,* 271: 795-9, 1996), with uniform flows (Perkins, T. T., et al., "Stretching of a single tethered polymer in a uniform flow," *Science,* 268: 83-7, 1995), with uniform electric fields (Ferree, S., et al., "Electrokinetic stretching of tethered DNA," *Biophys. J.,* 85(4):2539-46, 2003), using acoustic force spectroscopy (AFS) (Sitters, G., et al., "Acoustic force spectroscopy," *Nat. Methods,* 12(1):47-50, 2015), forcing DNA into a nanochannel (Tegenfeldt, J. O., et al., "The dynamics of genomic-length DNA molecules in 100-nm channels," *Proc. Natl. Acad. Sci. U.S.A.,* 101(30):10979-83, 2004), hydrodynamic focusing of multiple streams (Wong, P. K., et al., "Deformation of DNA molecules by hydrodynamic focusing," *J. Fluid. Mech.,* 497:55-65, 2003), and dynamic combing onto a surface (Dimalanta, E. T., et al., "A microfluidic system for large DNA molecule arrays," *Anal. Chem.,* 76(18):5293-301, 2004).

Figure 2:
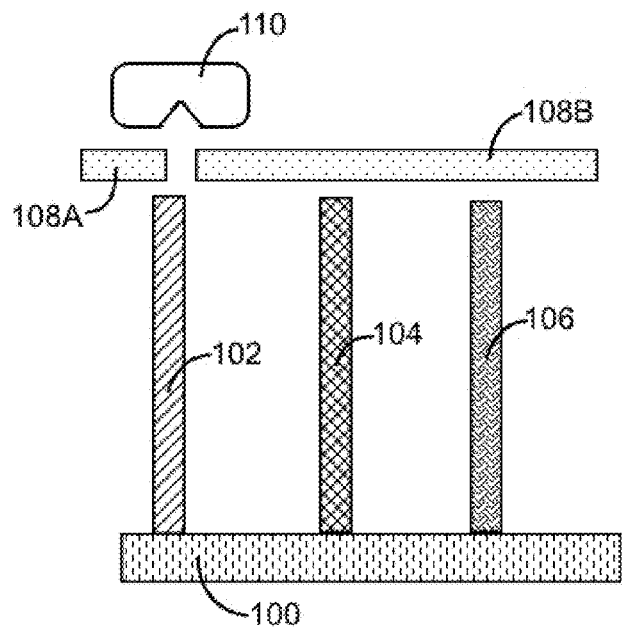
FIG. 2 depicts a schematic drawing of the action of a restriction enzyme during genomic library construction using vanishing and appearing restriction site ligation according to the present disclosure.

Turning now to FIG. 2, an action of a first restriction enzyme 110 is illustrated. The first restriction enzyme 110 can cut the stretched DNA 108 into DNA fragments of 108A and 108B at the restriction site recognized by the first restriction enzyme 110.

Figure 3:
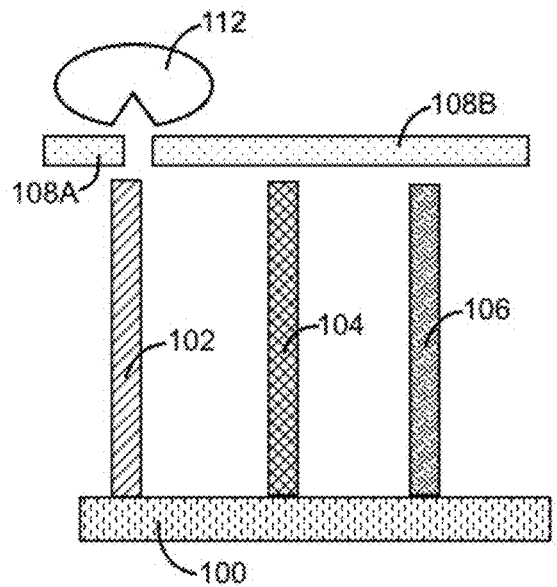
FIG. 3 shows a schematic drawing of the action of a ligase during genomic library construction using vanishing and appearing restriction site ligation according to the present disclosure.
Figure 4:
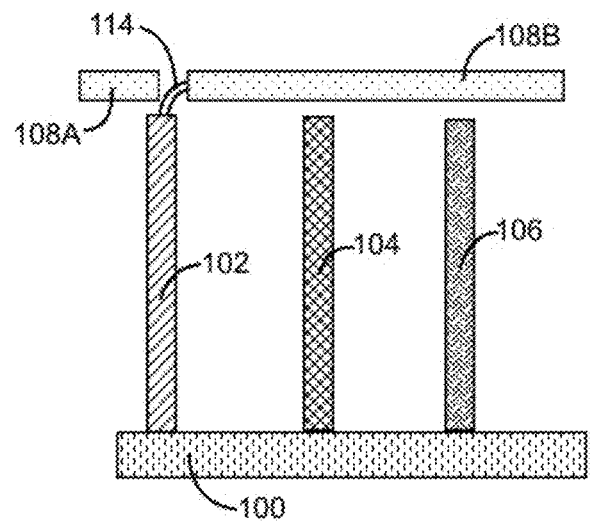
FIG. 4 exhibits a schematic drawing of a possible ligation product during genomic library construction using vanishing and appearing restriction site ligation according to the present disclosure.

After the DNA 108 is cut, as shown in FIG. 3, a ligase 112 may either re-ligate the two DNA fragments 108A and 108B back into DNA 108 as shown in FIG. 1, or may ligate one of the DNA fragment, for example, 108B, with an adapter, for example, adapter 102 via a covalent bond 114, to give a ligated product as shown in FIG. 4.

One advantage of the enzyme cocktail system according to the present disclosure is that it drives vanishing and appearing restriction sites within both the genomic DNA and among the adapters. These vanishing and appearing restriction sites in turn drive the formation of genomic fragments with attached adapters on both ends of the fragments.

On the one hand, the enzyme cocktail system creates vanishing and appearing restriction sites within the genomic DNA. First, because the genomic DNA is long, there are many restrictions sites available for digesting by the first restriction enzyme 110. With the choice of the length of the restriction site, one can control the average length of the resulting DNA fragments, as discussed above. When the genomic DNA is cut, the restriction sites are vanishing in numbers. Second, if the DNA fragments are ligated by the ligase, the same restriction site is recreated and remains intact. Therefore, this reappearing restriction site can still be cut by the first restriction enzyme. Third, over time, the DNA fragments generated will be ligated to adapters. Such ligation permanently destroys the restriction site for the first restriction enzyme and makes restriction sites for the first restriction enzyme vanishing permanently as the ligated adapter-DNA fragments are formed. This is caused by the design of the adapter sequence so that the newly generated adapter-DNA fragment sequence does not present an appearing restriction site for the first restriction enzyme or the second restriction enzyme.

On the other hand, the enzyme cocktail system creates vanishing and appearing restriction sites among the adapters. Specifically, the ligase may ligate two adapters and make them unavailable to the desired ligation with DNA fragments. However, due to the design of the adapters, the self-ligated adapters present an appearing restriction site for the second restriction enzyme, which, by design, recognizes a longer restriction site than the first restriction enzyme. Therefore, the appearing longer restriction site in the self-ligated adapters can be cut by the second restriction enzyme, thereby resulting in the vanishing of these longer restriction sites. In addition, once an adapter is ligated to a DNA fragment, that adapter forever ceases to be available for self-ligation with another adapter, and as a consequence the available longer restriction sites for the second restriction enzyme will be vanishing permanently as the ligated adapter-DNA fragments are formed.

Overall, relying on the vanishing and appearing restriction sites on or in-between adapters and a genomic DNA and its fragments, the enzyme cocktail shifts the equilibrium of the whole system toward the formation of genomic fragments with and attached adapter on both ends of the fragments.

Figure 5:
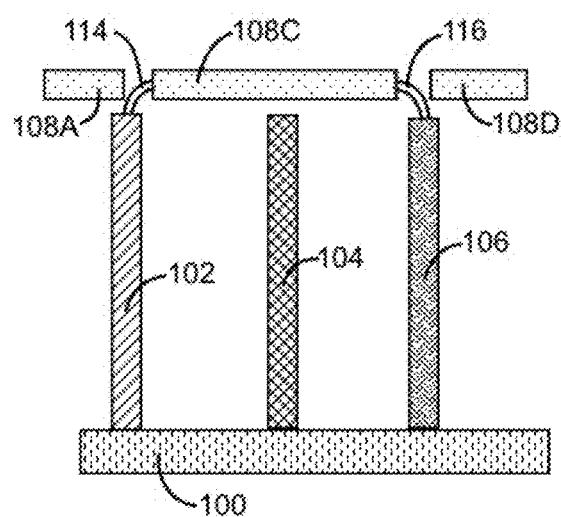
FIG. 5 displays a schematic drawing of another possible ligation product during genomic library construction using vanishing and appearing restriction site ligation according to the present disclosure.

Processes of digesting and ligating shown in FIGS. 2-4 can be repeated multiple times to give a DNA fragment ligated at both ends by adapters, for example, a DNA fragments 108C ligated to adapters 102 and 106 in FIG. 5, in which the DNA fragment 108C forms a covalent bond 114 with adapter 102 and a covalent bond 116 with adapter 106. The other DNA fragments 108A and 108D can undergo similar processes shown in FIGS. 2-5 and provide other adapter ligated DNA fragments to construct a DNA library, for example, a genomic DNA library.

Figure 6:
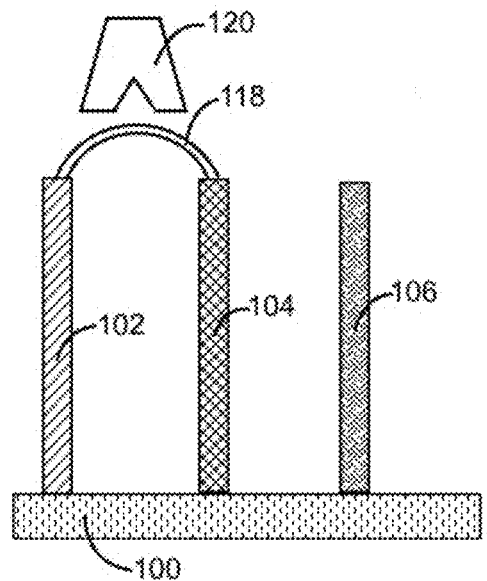
FIG. 6 illustrates a schematic drawing of still another possible ligation product during genomic library construction using vanishing and appearing restriction site ligation according to the present disclosure.

FIG. 6 is a schematic showing of another possibility in the presence of the ligase 112, which may ligate two adapters to form a covalent bond 118 in-between the two adapters 102 and 104. A second restriction enzyme 120 can cut the covalent bond 118 between the two adapters 102 and 104 so that both regenerated adapters 102 and 104 become available for ligation with other DNA fragments. The end results of the above processes are the creation of a DNA fragments library with each fragment bonded with adapters on both ends.

Figure 7:
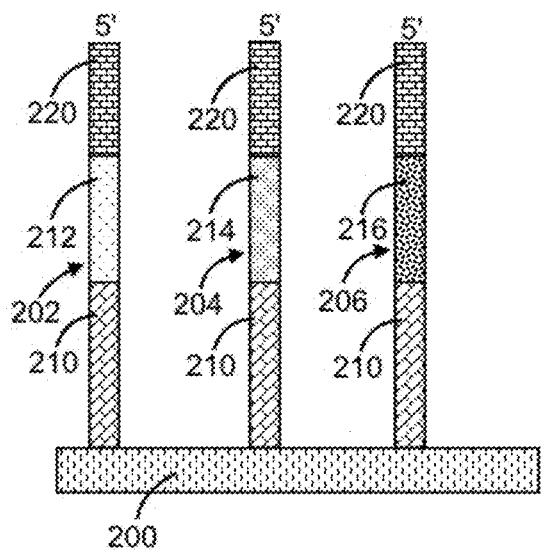
FIG. 7 depicts a schematic drawing of an exemplary initial setup of a chip with a single-stranded backbone for a Y-adapter according to the present disclosure.

A more detailed example of the systems and methods of the present disclosure are shown in FIGS. 7-12. Referring now to FIG. 7, the construction of the DNA library starts with the covalent attachment of single-stranded Y-adapter backbones 202, 204, and 206 to chip 200 via their 3' ends. The sequence of Y-adapter backbone 202 starting from the 3' end is Flow Cell 2' 210, Barcode 212 and Sequence Primer 2' 220. The sequence of Y-adapter backbone 204 starting from the 3' end is Flow Cell 2' 210, Barcode 214 and Sequence Primer 2' 220. The sequence of Y-adapter backbone 206 starting from the 3' end is Flow Cell 2' 210, Barcode 216 and Sequence Primer 2' 220.

Figure 8:
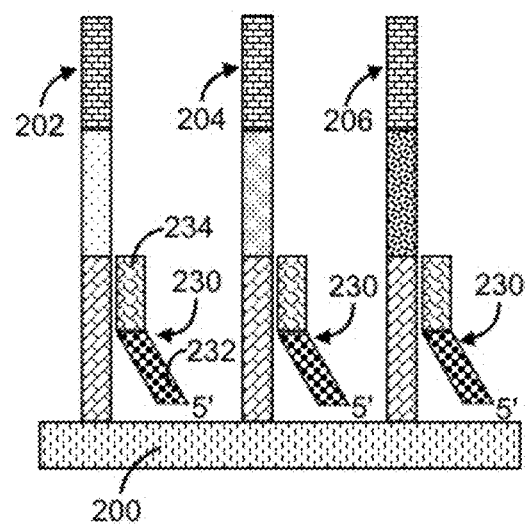
FIG. 8 shows a schematic drawing of hybridization of Y-adapter primer onto the backbone in FIG. 7 according to the present disclosure.

As depicted in FIG. 8, a Y-adapter primer 230 can hybridize to Flow Cell 2' 210 of Y-adapter backbones 202, 204, and 2006. The sequence of Y-adapter primer 230 starting from the 5' end is Y-stem 232, and Flow Cell 2' complementary fragment 234, wherein Flow Cell 2' complementary fragment 234 hybridizes with the complementary section of Flow Cell 2' 210 of Y-adapter backbones 202, 204, and 206.

Figure 9:
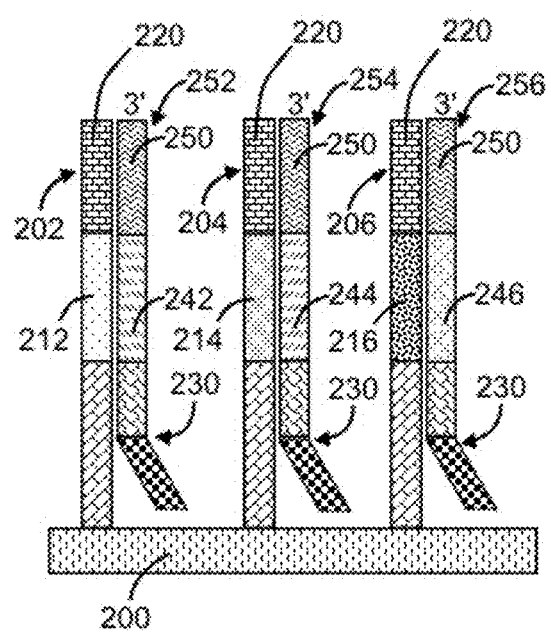
FIG. 9 exhibits a schematic drawing of extension of the Y-adapter primer in FIG. 8 through the backbone according to the present disclosure.

As demonstrated in FIG. 9, the hybridized Y-adapter primer 230 can be extended over the barcode region and the sequence primer region of each bound Y-adaptor backbone. Specifically, Y-adapter primer 230 hybridized on Y-adapter backbone 202 is extended from its 3' end with Barcode 242 complementary to 212 and Sequence Primer 2 250 complementary to 220 to give a complete Y-adapter Y-strand 252. Y-adapter primer 230 hybridized on Y-adapter backbone 204 is extended from its 3' end with Barcode 244 complementary to 214 and Sequence Primer 2 250 complementary to 220 to give a complete Y-adapter Y-strand 254. Y-adapter primer 230 hybridized on Y-adapter backbone 206 is extended from its 3' end with Barcode 246 complementary to 216 and Sequence Primer 2 250 complementary to 220 to give a complete Y-adapter Y-strand 256. At this stage, the chip 200 is modified with multiple Y-adapters composed of Y-adapter backbone and Y-adapter Y-strand: 202/252 strands, 204/254 strands, and 206/256 strands.

Figure 10:
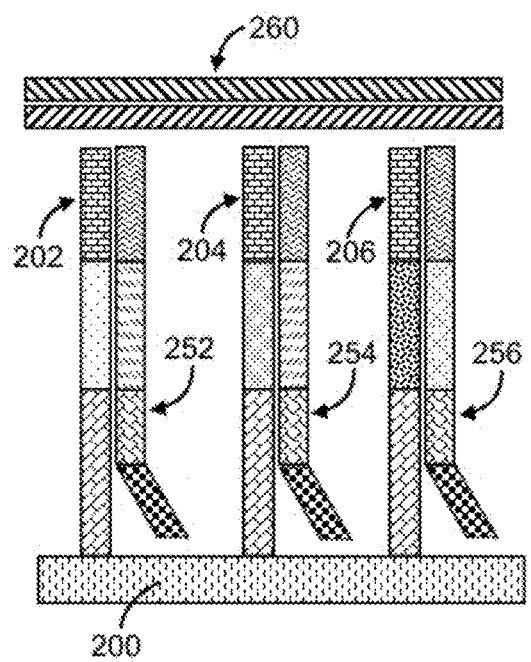
FIG. 10 displays a schematic drawing of stretching a genomic DNA over a Y-adapter chip according to the present disclosure.
Figure 11:
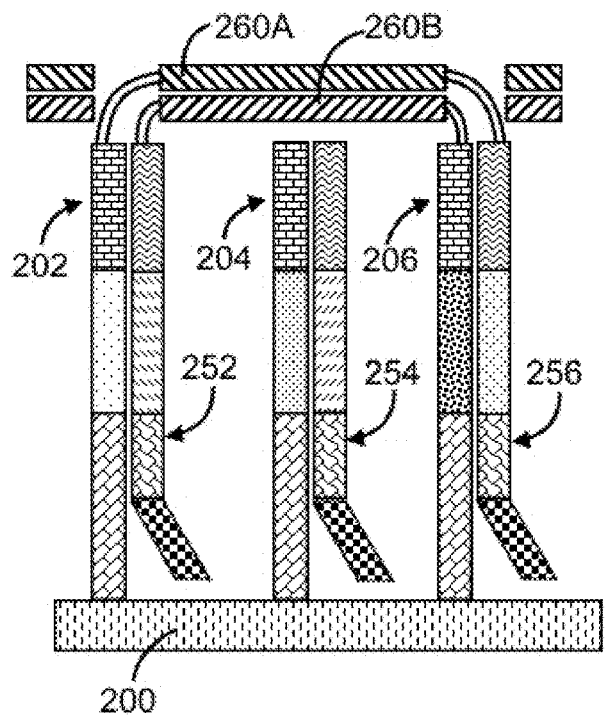
FIG. 11 illustrates a schematic drawing of a digested and ligated genomic DNA on the Y-adapter chip according to the present disclosure.

A Genomic DNA 260 is then placed on and stretched over the surface of Y-adapters 202/252, 204/254, and 206/256, as shown in FIG. 10. In the presence of an enzyme cocktail and with the help of vanishing and appearing restriction sites for ligation according to the present disclosure, Genomic DNA 260 can be digested by the first restriction enzyme to produce multiple fragments, one of which may consist of Genomic DNA fragment strands 260A and 260B, as depicted in FIG. 11. With the help of the ligase and the second restriction enzyme, Genomic DNA fragment strand 260A may be ligated to Y-adapter backbone 202 on its 3' end and to Y-adapter Y-stem 256 on its 5' end. Likewise, Genomic DNA fragment strand 260B may be ligated to Y-adapter backbone 206 on its 3' end and to Y-adapter Y-stem 252 on its 5' end.

Figure 12:
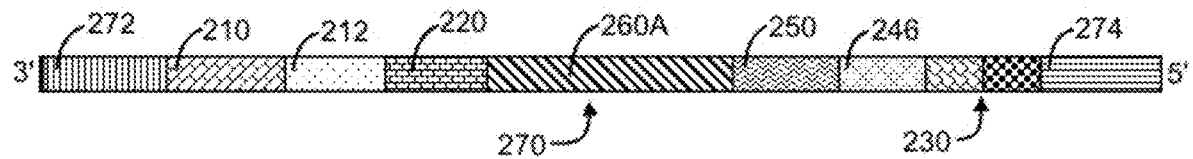
FIG. 12 depicts a schematic drawing of a PCR product using Illumina adapters 1 and 2 with the digested and ligated DNA in FIG. 11 according to the present disclosure.

Turning now to FIG. 12 and focusing on Genomic DNA fragment strand 260A, other adapters for NGS sequencing, for example, Illumina Adapters 1 and 2, can be added at this stage and PCR reactions can be run with DNA fragments thus obtained to produce PCR product 270. The sequence of PCR product 270 starting from the 3' end is Illumina Adapter 1 272, Flow Cell 2' 210, Barcode 212, Sequence Primer 2' 220, Genomic DNA fragment 260A, Sequence Primer 2 250, Barcode 246, Y-adapter primer 230 (which consists of Flow Cell 2' complementary fragment 234 and Y-stem 232) and Illumina Adapter 2 274. As demonstrated by PCR product 270, Genomic DNA fragment 260A now has asymmetrical end sequences with two different barcodes. Such a composition of Genomic DNA fragment 260A can give positional information of the starting Genomic DNA 260.

Figure 13:
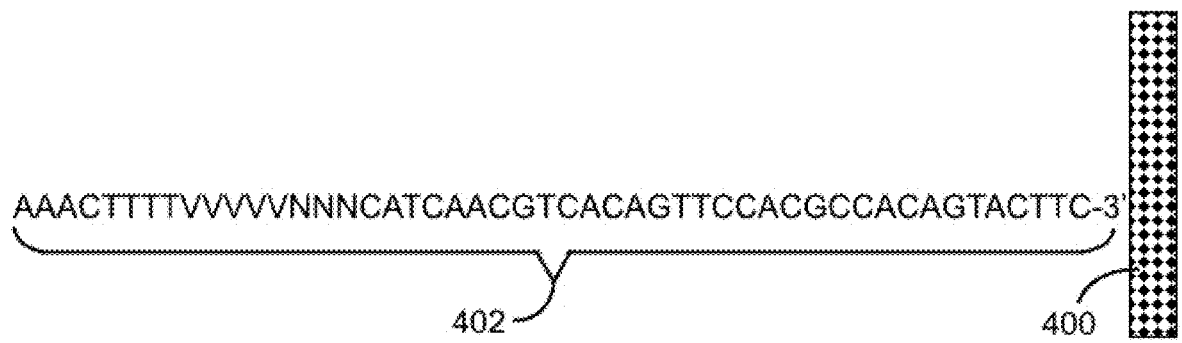
FIG. 13 shows a Y-adapter backbone (SEQ ID NO: 3) having a specific sequence on a Y-adapter chip according to the present disclosure.

Another detailed example of the systems and methods of the present disclosure, especially the design of Y-adapters, are shown in FIGS. 13-17. Turning now to FIG. 13, the construction of the DNA library starts with the covalent attachment of single-stranded Y-adapter backbone 402 to chip 400 via the 3' end of the Y-adapter backbone 402.

Figure 14:
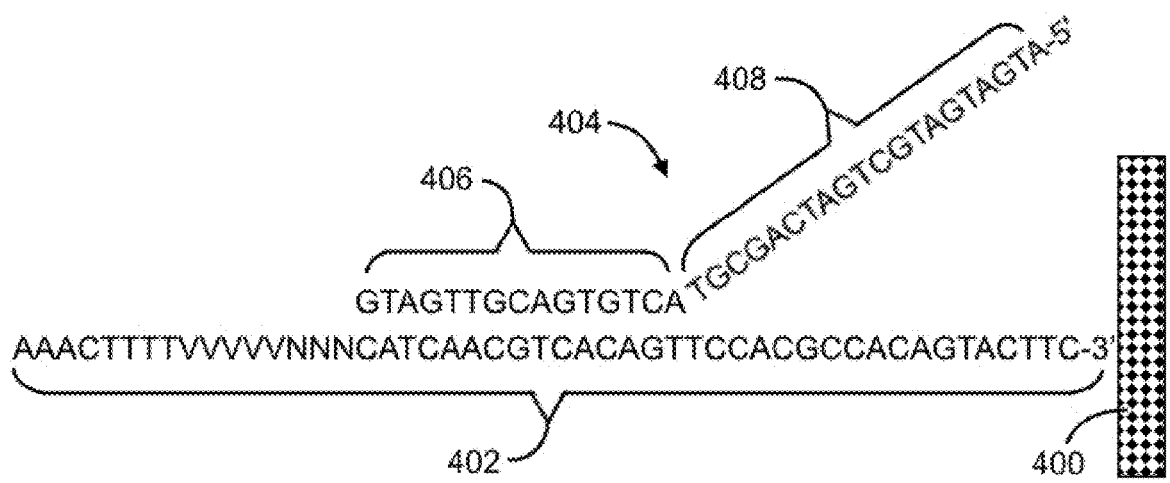
FIG. 14 exhibits hybridization of Y-adapter primer (SEQ ID NO: 4) having a specific sequence onto the backbone (SEQ ID NO: 3) in FIG. 13 according to the present disclosure.

Referring to FIG. 14, a Y-adapter primer 404 can hybridize to Y-adapter backbone 402. The sequence of Y-adapter primer 404 starting from the 5' end is SEQ C 408, and SEQ A' 406, wherein SEQ A' 406 hybridizes with the complementary section of Y-adapter backbone 402.

As demonstrated in FIG. 15, the hybridized Y-adapter primer 404 can be extended over Y-adaptor backbone 402 to give Y adapter Y-strand 410. Specifically, Y-adapter primer 404 hybridized on Y-adapter backbone 402 is extended from its 3' end with sequence 412. At this stage, the chip 400 is modified with multiple Y-adapters, including Y-adapter 460, which composes Y-adapter backbone 402 and Y-adapter Y-strand 410.

FIG. 16 shows the complete anatomy of the obtained Y-adapter 460. The Y-adapter 460 consists of two strands: Y-adapter backbone 402 and Y-adapter Y-strand 410. The sequence of Y-adapter backbone 402 starting from the 5' end comprises one half of the restriction site for Pme1 422, barcode termination signal 424, barcode sequence 426 (wherein V represents any of A, C, or G, and N represents any of A, T, C and G), SEQ A 428, and SEQ B 430. The sequence of Y-adapter Y-strand 410 starting from the 3' end comprises the other half of the restriction site for Pme1 434, barcode termination signal 436, barcode sequence 438, SEQ A' 440, and SEQ C 442. As discussed above, the sequence of 5'-GTTTAAAC-3' is the restriction site for Pme1 restriction enzyme. Therefore, if two Y-adapters 460 self-ligate, the ligated product contains the sequence of 5'-GTTTAAAC-3' at the joint, thereby becoming a substrate for the Pme1 restriction enzyme to cut.

The following are two PCR primers, which are designed to interface with the different 5' and 3' sequences on the ends of Y-adaptor 460 and which introduce Illumina Flowcell sequences (FC1 and FC2 shown in non-bold):

(SEQ ID NO: 1)
AATGATACGGCGACCACCGAGATCTACACATGATGATGCTGATCAG

CGT-3'

(SEQ ID NO: 2)
CAAGCAGAAGACGGCATACGAGATGAAGTACTGTGGCGTGG-3'

After digestion of the Genomic DNA and ligation of the Genomic DNA fragments to the Y-adapters according to the present disclosure, PCR of thus-obtained Genomic DNA fragments from FIG. 16 using the PCR primers disclosed above can give the products shown in FIG. 17 after at least two rounds of PCR. These PCR products of the Genomic DNA fragments library can be further processed by sequencing processes, for example, by Illumina sequencing processes.

Figure 18:
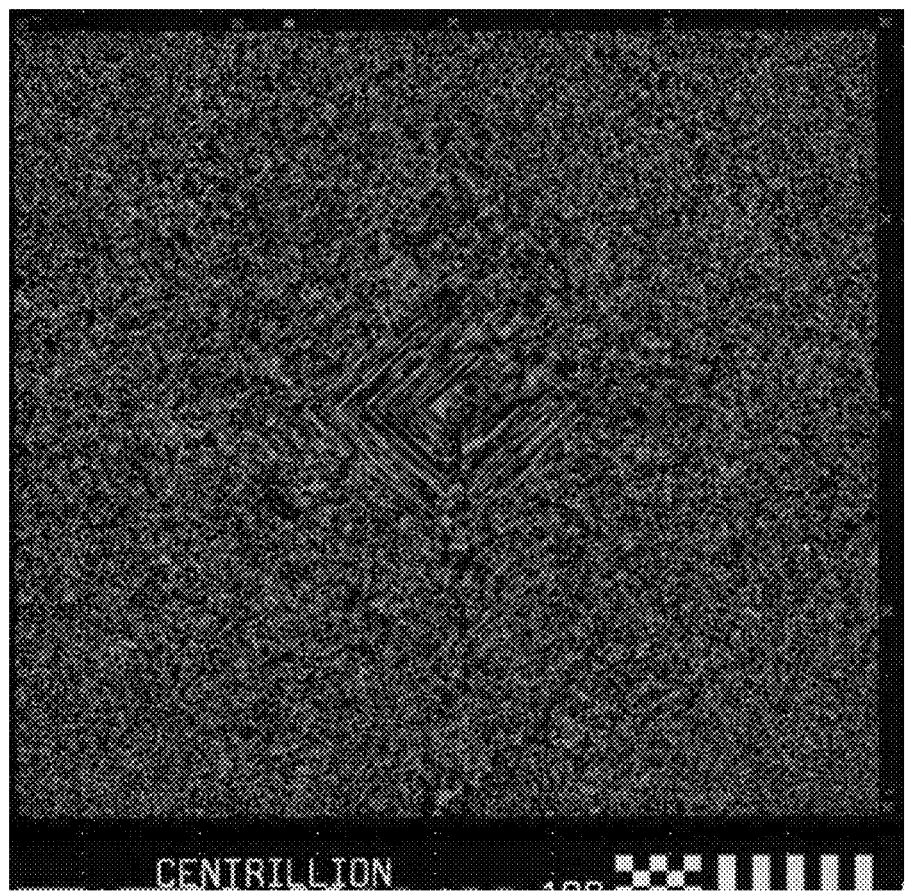
FIG. 18 shows features of the patterned array on a chip according to the present disclosure.

Referring to FIG. 18, the chip according to the present disclosure can have patterned array with millions of barcoded features as shown in FIG. 18. These barcoded features can have identifiable locations on the chip and their barcodes (embedded in the corresponding Y-adapters) can be designed to reflect their identifiable locations. After these barcodes are ligated to Genomic DNA fragments, each fragment can carry with it information about identifiable locations where the ends of the DNA fragment were lying on the chip. Because the Genomic DNA is stretched over arrays of Y-adapters, the identifiable location information associated with different Genomic DNA fragments can present information related to the relative distance between the Genomic DNA fragments and the orientation of the Genomic DNA. Therefore, the systems and methods in the present disclosure can identify position and vector of genomic DNA.

III. EXAMPLES

1. Chip Capacitance Set-Up

A Y-adapter loaded gel was placed between the parallel copper plates with 0.5 μs human genomic DNA in the cis-solution. A voltage potential of 50 mV was applied to the parallel copper plates for 2 minutes.

Figure 19:
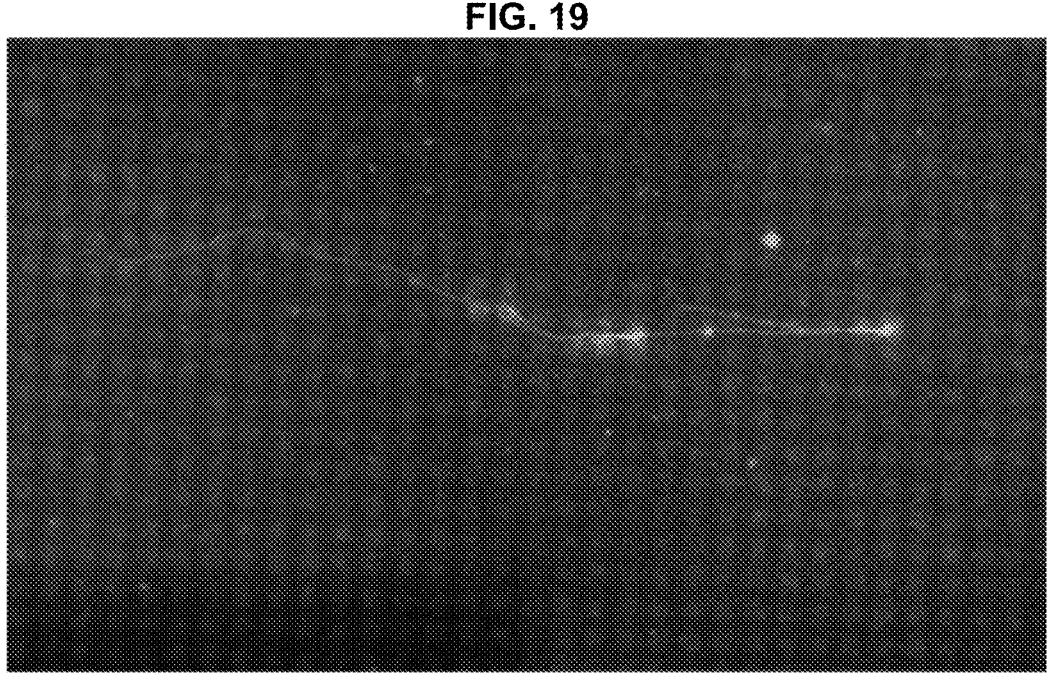
FIG. 19 exhibits a genomic DNA stretched on a Y-adapter chip according to the present disclosure.

FIG. 19 depicts a picture of a DNA stretched using the above-described chip capacitance set-up. The uncoiled DNA was visibly stretched over the surface.

2. Digestion and Ligation Using Vanishing and Appearing Restriction Sites

After capacitance application of genomic DNA to the gel, a mixture of enzymes comprising Alu1 restriction enzyme, T4 DNA ligase and Pme1 restriction enzyme, and buffers were applied to the gel obtained above. As comparison, a control experiment in which the Pme1 restriction enzyme was omitted from the above enzyme mixture was also conducted. Digestion of the stretched genomic DNA with Alu1 and ligation of the DNA fragments with T4 DNA ligase to the Y-adapters loaded gel formed the library. After this enzyme treatment, the gel was scraped into a PCR tube for initial analysis.

Figure 20:
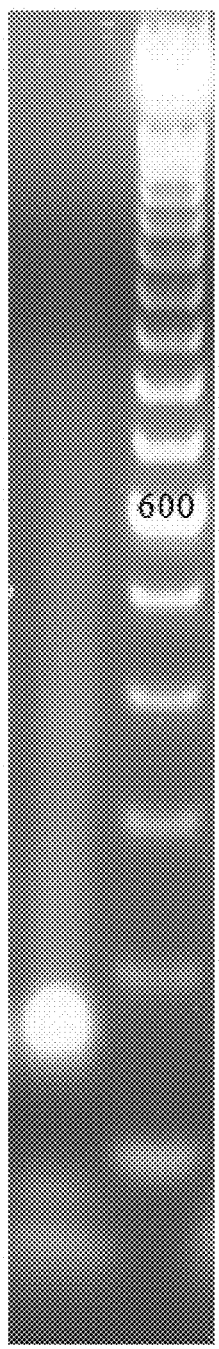
FIG. 20 displays gel pictures of PCR products derived from methods according to the present disclosure.
Figure 20:
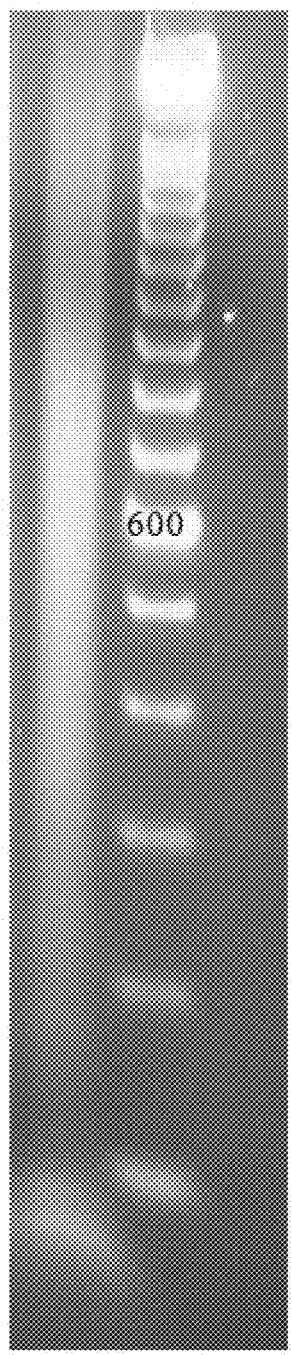
Figure 20:
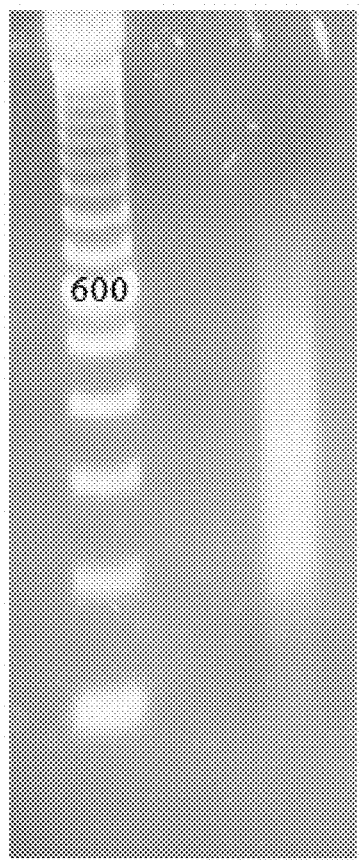

FIG. 20 displays agarose gel electrophoresis pictures of the PCR products obtained after digestion and ligation using vanishing and appearing restriction sites. Lane 1 corresponds to PCR products obtained from a DNA fragments library after 5 PCR cycles from Y-adapter/DNA capacitance gel without the addition of Pme1 restriction enzyme. The bright spot in Lane 1 near the bottom corresponds to self-ligated Y-adaptors. Lane 2 corresponds to PCR products obtained from a DNA fragments library in the presence of low salt Pme1 digestion of self-ligated Y-adapters followed by 20 PCR cycles. As compared with Lane 1, the bright spot corresponding to self-ligated Y-adapters disappeared in Lane 2. This observation suggests that the addition of the Pme1 restriction enzyme helped digestion of self-ligated Y-adapters and made the Y-adapters available for DNA fragments capture. In addition, comparison of Lanes 1 and 2 shows that the relative amount of DNA fragments vs. self-ligated Y-adapters increased as demonstrated by the increased intensity of bands spreading above the self-ligated Y-adaptor spot in Lane 2 than in Lane 1. Lane 3 corresponds to PCR products after size selection and clean-up of a DNA fragments library similar to what was obtained in Lane 2. The selected sizes were from 200 bp to 600 bp. The library concentration was 6 nM and was ready for sequencing on the MiSeq machine. If by design, the self-ligated Y-adapters are about 100 bp in length, a downstream size selection step after the library construction can remove the ligated Y-adapters still remained in the crude library by setting the selection size over a pre-determined number, for example, 150 bp, 200 bp, or 250 bp.

Figure 21:
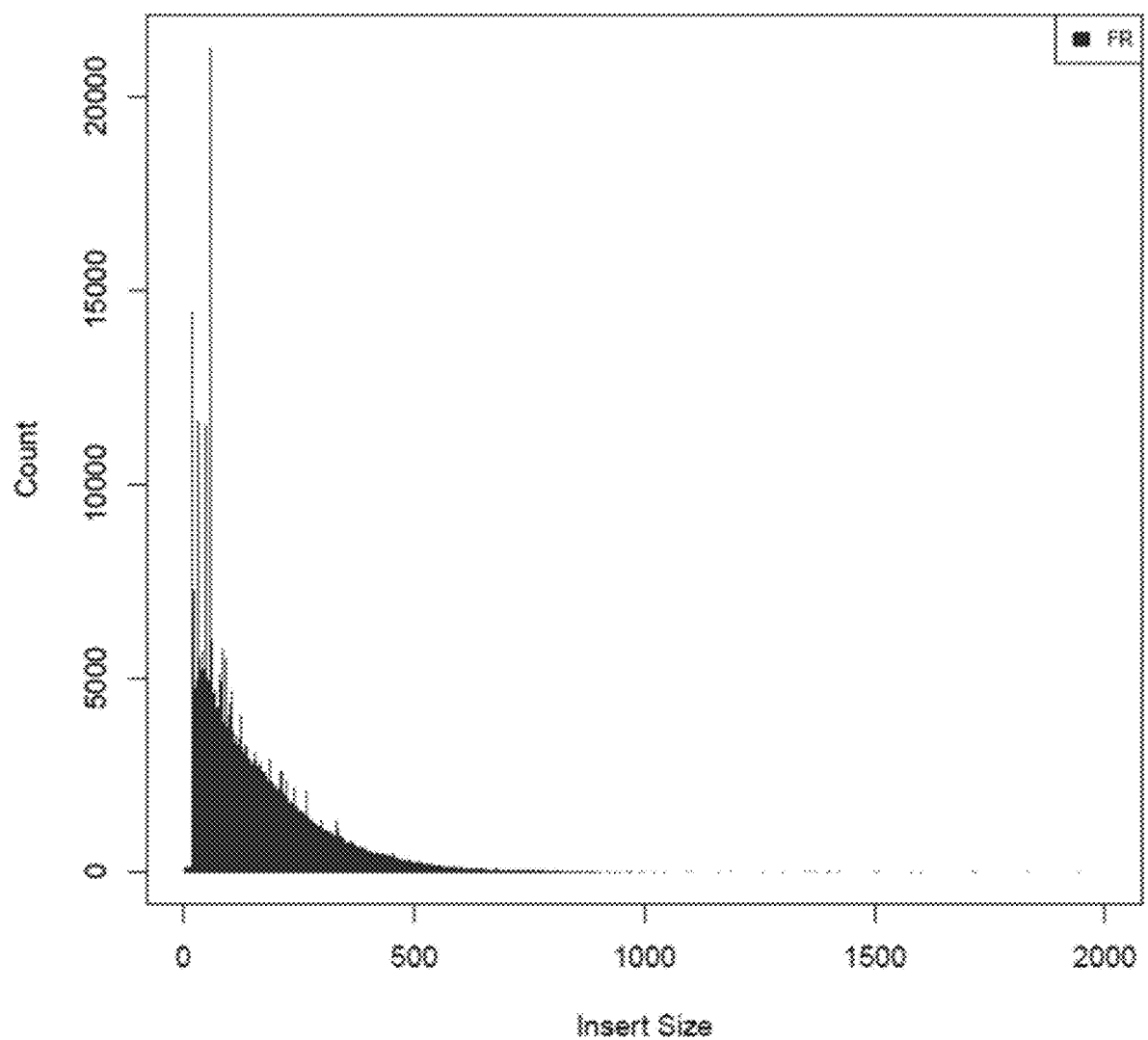
FIG. 21 illustrates distribution of fragment sizes of a genomic DNA in a library constructed using methods according to the present disclosure.
Figure 22:
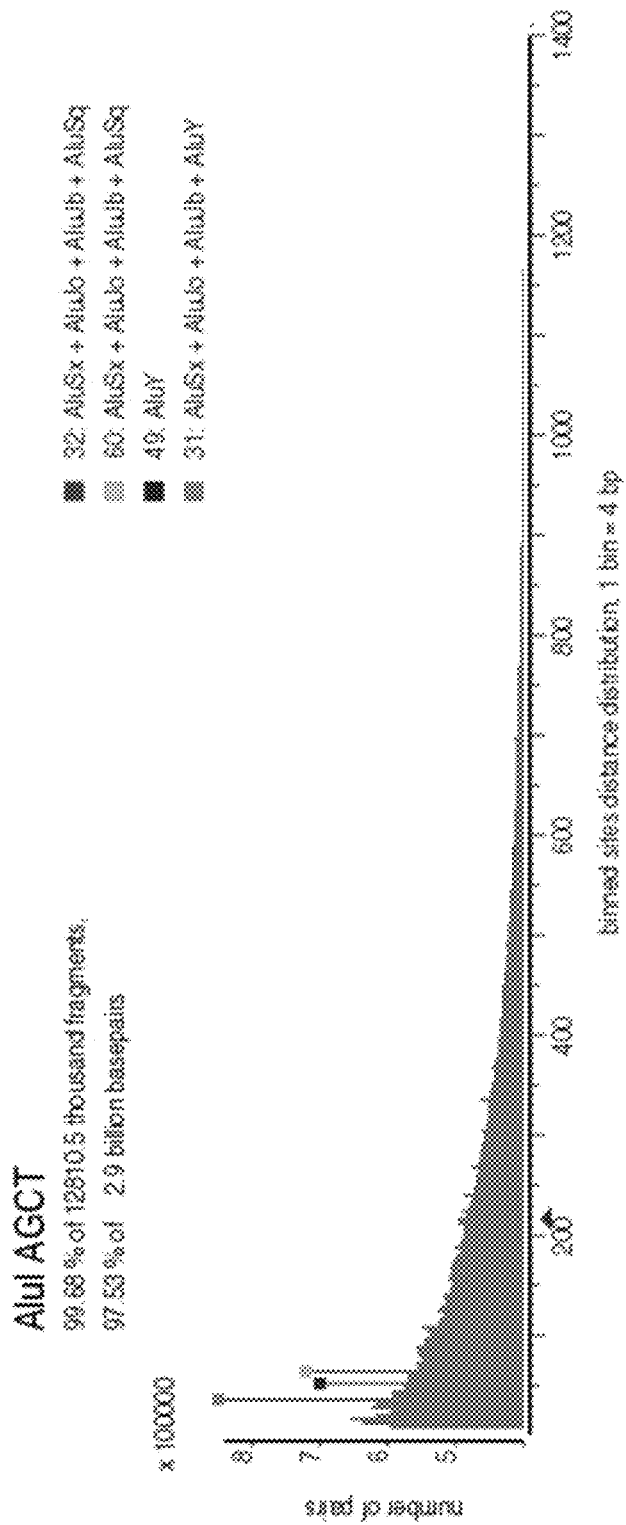
FIG. 22 depicts calculated, theoretical distribution of fragment sizes of the library in FIG. 21.

FIG. 21 showed the distribution of DNA fragment sizes in a library obtained using Alu1 digestion and sequencing. FIG. 22 depicts the theoretical distribution of fragment sizes for the same genomic DNA used in FIG. 21 after Alu1 digestion according to New England BioLabs, Inc. Comparison of FIGS. 21 and 22 shows that the theoretical prediction matched well with the experimental results obtained.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

3. Experimental Details for Stretching and Assembling a Genomic Library on a Chip Using Y Adapters and Vanishing Restriction Sites A barcoded chip array with an oligonucleotide 402 was synthesized as shown in FIG. 13. The adapter oligonucleotide 404 was suspended at a concentration of 5 μM in 10×SSC buffer supplemented with 25 mM MgCl$_2$.

Fifty microliter of the oligonucleotide 404 solution was deposited on the chip array, placed in a humidified chamber to prevent evaporation, and incubated for 5 hours at 50° C.

The humidified chamber was removed from the incubator and allowed to cool to room temperature. Then the chip array was rinsed two times with 4×SSC, then two times with 2×SSC, then two times with 0.5×SSC. Each rinse buffer had been prechilled to 4° C. Finally, the chip array was soaked in 1 mL of 1× Thermopol Buffer so as to equilibrate the hybridized oligonucleotides 402 and 404 and prepare them for extension by BST polymerase.

A 50 μl solution of 1× Thermopol Buffer, 20 mM dNTP's, and 10 units of BST Polymerase Large Fragment (all reagents purchased from New England Biolabs) was deposited onto the hybridized chip array and allowed to incubate at 50° C. for 3 hours in a humidified chamber.

The now extended, double stranded chip array with double-stranded DNA was washed 4 times in ice cold IVIES buffer (50 mM, pH 5.5) and human genomic DNA was prepared for stretching onto the array.

Human Genomic DNA was purchased from Promega and diluted in IVIES buffer (50 mM, pH 5.5) to a final concentration of 50 pg/µl. Next, 1.25 mL of the genomic DNA solution was transferred to a stretching cuvette. The chip array was clipped onto a stretching machine and submerged into the genomic DNA solution in the cuvette for 1 hour.

Just before retraction of the array, an electric field was applied perpendicular to the plane of the chip array by using two copper plates connected to a voltage source as parallel plate capacitors. The calculated strength of the electric field was 22,500 Newtons/coulomb. Once the electric field was turned on, the array was retracted from the genomic DNA solution in the cuvette at a rate of 67 µm/sec.

The array was then allowed to incubate in ice cold Cutsmart buffer to remove any residual MES buffer from the stretching.

A 120 µL enzyme cocktail was prepared as follows: 84 µl $H_2O$, 12 µL Cutsmart buffer, 12 µL ATP (final concentration 10 mM), 6 µL (60 units) of Alu1 restriction enzyme, 4 µL (40 units) of T4 DNA ligase, 2 µL (20 units) of Pme1 restriction enzyme giving a final ratio of 3:2:1 Alu1:T4:Pme1.

The enzyme cocktail (120 µL) was placed on the hybridized and extended array with stretched DNA on it and allowed to incubate at 37° C. for 2 hours. This was the reaction that allows vanishing and appearing restriction sites to form the library.

The library now ligated to the chip array was rinsed 3 times in ice cold Cutsmart buffer.

The chip array was placed into a PCR tube or, alternatively, a slide PCR reaction can be set up. After 5 cycles of PCR, (using the primers that interface with the two different ends of the Y adapter and include Illumina flow cell sequences on the ends, as shown above after the description of FIG. 16), a quick Pme1 digestion was conducted in low salt (0.5× Cutsmart buffer) for 30 minutes at 37° C. to digest any self-ligated Y adapters that were not cut during the previous ligation/digestion reaction with the genomic DNA. Lane 1 and Lane 2 in FIG. 20 showed gel pictures obtained before and after the Pme1 digestions from the same library.

Finally, the library was cleaned up and size selected using either by beads or by a gel extraction kit. For example, gel extraction kit from Qiagen was used to run the size selection and fragments selected from the library were ranging from 200-750 bp. A library after all of the above steps can range from 5-12 nM in concentration. The gel in Lane 3 of FIG. 20 showed a library of 6 nM in concentration, which can proceed with sequencing on the Illumina MiSEQ. The library was then prepared for the Illumina machine following the manufacturer's protocol.

What is claimed is:

1. A method for constructing a library from a nucleic acid, the method comprising:
   a) placing at least one double-stranded nucleic acid on a surface to which are attached a plurality of adapters, wherein each adapter comprises a double-stranded end;
   b) applying a solution to the surface, the solution comprising:
      i. a first restriction enzyme digesting the double-stranded nucleic acid into a plurality of double-stranded nucleic acid fragments;
      ii. a ligase ligating a first end of one member of the plurality of double-stranded nucleic acid fragments to the double-stranded end of a first adapter of the plurality of adapters, ligating a second end of the one member of the plurality of double-stranded nucleic acid fragments to the double-stranded end of a second adapter of the plurality of adapters, and ligating a third adapter and fourth adapter of the plurality of adapters to form self-ligated double-stranded adapters, wherein both strands of the one member of the plurality of double-stranded nucleic acid fragments are ligated to the first adapter at the first end and to the second adapter at the second end, respectively; and
      iii. a second restriction enzyme digesting the self-ligated double-stranded adapters; and
   c) forming a first library, the first library comprising a plurality of ligated double-stranded nucleic acid fragments comprising the one member of the plurality of nucleic acid fragments ligated with the first adapter and the second adapter.

2. The method of claim 1, wherein the placing at least one double-stranded nucleic acid on the surface comprises stretching the at least one double-stranded nucleic acid on the surface.

3. The method of claim 1, wherein the plurality of adapters are Y-shaped adapters.

4. The method of claim 1, wherein concentration of the first restriction enzyme is higher than concentration of the ligase in the solution.

5. The method of claim 1, wherein the self-ligated double-stranded adapters comprise a restriction site for the second restriction enzyme after the self-ligation.

6. The method of claim 1, wherein the first restriction enzyme recognizes 4 base pairs restriction site, 5 base pairs restriction site, or 6 base pairs restriction site.

7. The method of claim 6, wherein the first restriction enzyme is MspA1I restriction endonuclease, PsiI restriction endonuclease, or Alu1 restriction endonuclease.

8. The method of claim 1, wherein the ligase is T4 ligase.

9. The method of claim 1, wherein the first restriction enzyme recognizes a shorter sequence for the restriction site than the second restriction enzyme.

10. The method of claim 9, wherein the second restriction enzyme is Pme1 restriction endonuclease.

11. The method of claim 1, further comprising amplification of the first library, thereby producing a second library of amplified ligated nucleic acid fragments.

12. A method for constructing a library from a double-stranded target nucleic acid, the method comprising:
   a) placing the double-stranded target nucleic acid on a surface, wherein the surface comprises a plurality of adapters comprising a first adapter comprising a first double-stranded end and a second adapter comprising a second double-stranded end;
   b) treating the double-stranded target nucleic acid on the surface with a mixture of enzymes comprising a restriction enzyme and a ligase, the treating comprising:
      i. digesting the double-stranded target nucleic acid into a plurality of double-stranded nucleic acid fragments comprising a first double-stranded nucleic acid fragment; and
      ii. ligating both strands of the first double-stranded nucleic acid fragment with the first adapter at the first double-stranded end and with the second adapter at the second double-stranded end, thereby forming a first ligated double-stranded nucleic acid fragment; and
   c) forming a first library comprising a plurality of ligated double-stranded nucleic acid fragments comprising the first ligated double-stranded nucleic acid fragment.

13. The method of claim 12, wherein the digesting the double-stranded target nucleic acid is by the restriction enzyme.

14. The method of claim 12, wherein the ligating both strands of the first double-stranded nucleic acid fragment with the first and second adapters is by the ligase.

15. The method of claim 12, further comprising: before c), digesting a self-ligated adapter nucleic acid, wherein the plurality of adapters comprising a third adapter comprising a third double-stranded end and a fourth adapter comprising a fourth double-stranded end, and wherein a ligase ligates the third and the fourth adapters at the third and the fourth double-stranded ends to form the self-ligated adapter nucleic acid.

16. The method of claim 15, wherein the mixture of enzymes further comprises another restriction enzyme, and wherein the digesting the self-ligated adapter nucleic acid is by the another restriction enzyme.

17. The method of claim 16, wherein the digesting the self-ligated adapter nucleic acid by the another restriction enzyme re-forms the third adapter and the fourth adapter.

18. The method of claim 16, wherein the self-ligated adapter nucleic acid comprises a restriction site for the another restriction enzyme after the ligating the third and the fourth adapters.

19. The method of claim 16, wherein the restriction enzyme is different from the another restriction enzyme.

20. The method of claim 12, wherein the placing the double-stranded target nucleic acid on the surface comprises stretching the double-stranded target nucleic acid on the surface.

* * * * *

SEQUENCE LISTING

```
<160> NUMBER OF SEQ ID NOS: 5

<210> SEQ ID NO 1
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
aatgatacgg cgaccaccga gatctacaca tgatgatgct gatcagcgt             49

<210> SEQ ID NO 2
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
caagcagaag acggcatacg agatgaagta ctgtggcgtg g                    41

<210> SEQ ID NO 3
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (14)..(16)
<223> OTHER INFORMATION: a, c, t, g, unknown or other

<400> SEQUENCE: 3 aaactttvv vvvnnncatc aacgtcacag ttccacgcca cagtacttc             49

<210> SEQ ID NO 4
```

```
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
atgatgatgc tgatcagcgt actgtgacgt tgatg                              35

<210> SEQ ID NO 5
<211> LENGTH: 51
<212> TYPE: DNA
<213> ORGANISM: Artificial Sequence
<220> FEATURE:
<223> OTHER INFORMATION: Description of Artificial Sequence: Synthetic
      primer
<220> FEATURE:
<221> NAME/KEY: modified_base
<222> LOCATION: (36)..(38)
<223> OTHER INFORMATION: a, c, t, g, unknown or other

<400> SEQUENCE: 5
atgatgatgc tgatcagcgt actgtgacgt tgatgnnnvv vvvaaaagtt t            51
```